United States Patent [19]

Maahs

[11] Patent Number: 4,501,275

[45] Date of Patent: Feb. 26, 1985

[54] MAMMALIAN SUBJECT HEATING UNIT USING RADIANT HEAT

[76] Inventor: Jerry D. Maahs, 19230 Glen Kerry Dr., Brookfield, Wis. 53005

[21] Appl. No.: 280,999

[22] Filed: Jul. 6, 1981

[51] Int. Cl.³ .................................................. A61F 7/00
[52] U.S. Cl. ........................................ 128/402; 128/399
[58] Field of Search ............... 128/373, 402, 1 B, 371, 128/399

[56] References Cited

U.S. PATENT DOCUMENTS

| | | | |
|---|---|---|---|
| 558,394 | 4/1896 | Kellogg. | |
| 664,081 | 12/1900 | Gohlin. | |
| 670,668 | 3/1901 | Hadaway, Jr.. | |
| 703,826 | 7/1902 | Randall | 128/402 |
| 791,232 | 5/1905 | Wolpers et al.. | |
| 861,744 | 7/1907 | Marsh. | |
| 1,051,349 | 1/1913 | Neitro. | |
| 1,968,015 | 7/1934 | Cooke et al. | 128/373 |
| 2,012,221 | 8/1935 | Clark et al. | 174/177 |
| 2,068,612 | 1/1937 | Sittler | 128/373 |
| 2,086,827 | 7/1937 | Smith | 219/36 |
| 2,096,128 | 10/1937 | Mortrude, Jr. | 128/373 |
| 2,098,295 | 11/1937 | Kettering et al. | 128/373 |
| 2,098,316 | 11/1937 | Sittler | 128/373 |
| 2,223,669 | 12/1940 | Forshee et al. | 128/373 |
| 2,289,881 | 7/1942 | Mallory et al. | 128/373 |
| 2,298,046 | 10/1942 | Emerson | 128/373 |
| 2,501,989 | 3/1950 | Burns et al. | 128/373 |
| 2,856,501 | 10/1958 | Kueser | 219/35 |
| 3,412,234 | 11/1968 | Otavka | 219/406 |
| 4,100,415 | 7/1978 | Blaisdell et al. | 128/371 |

*Primary Examiner*—C. Fred Rosenbaum
*Assistant Examiner*—C. W. Shedd
*Attorney, Agent, or Firm*—Andrus, Sceales, Starke & Sawall

[57] ABSTRACT

A heating unit using radiant heat provides core temperature increases in mammalian subjects, including humans, for cancer treatment or other purposes. The unit has a wall member defining a cavity for receiving the subject. An electric heating cable is placed on the exterior of the wall means for heating the wall means and radiating heat to the subject. A circuit is connectable to a source of electric power for energizing and controlling the heating cables.

23 Claims, 7 Drawing Figures

MAMMALIAN SUBJECT HEATING UNIT USING RADIANT HEAT

The present invention relates to a heating unit for live mammalian subjects, including humans. The unit employs radiant heat to increase internal temperatures, including increases to elevated levels considered to have a therapeutic effect on cancer.

Cancer is currently treated by surgery, radiation, chemotherapy, immunotherapy, or combinations of the foregoing. However, there is an increasing recognition that hyperthermia—a condition of greatly elevated body temperature—may provide significant therapeutic effects on cancer, including that not responsive or amenable to conventional treatment. Hyperthermic treatment of cancer involves raising the temperature of the patient to 41.8°–42° C. (approximately 107° F.) and maintaining that temperature for a predetermined period of time. The entire body of the patient is usually heated so that the technique has become known as "whole body hyperthermia." Hyperthermia is typically used in combination with other treatment such as chermotherapy or radiation.

To date, a variety of techniques have been used to produce the hyperthermia condition. These techniques include immersing the patient in hot wax; placing the patient in a suit or under a blanket containing ducts for heated fluid; withdrawing blood from the body, heating it, and returning it to the body; diathermy in which an R-F coupling is established between the body and a high frequency energy source; and applying ultrasonic energy to the patient. However, such approaches exhibit one or more limitations or shortcomings. These include the need for general anesthesia with the attendant medical risk, the need for specialized personnel and/or facilities, the danger of burns to the patient due to heat concentration of hot spots in the equipment, the possibility of blood damage to the patient, extensive and complex temperature monitoring and regulation apparatus, prolonged heating times, and cumbersomeness of the equipment.

Further, inasmuch as hyperthermia is carried out at temperatures only slightly below those that can cause death, the operating characteristics of the apparatus used to establish and maintain the hyperthermic condition can be extremely critical.

It is, therefore, the object of the present invention to avoid the shortcomings of the above techniques and provide improved apparatus for effectively and accurately raising the internal or core temperature of live animals, particularly mammalian subjects including humans, to a desired level with a commensurate degree of safety.

By contrast to the approaches heretofore taken, the apparatus of the present invention utilizes radiant heat. Briefly, the present invention contemplates apparatus having a wall member defining a cavity appropriate for receiving the subject. A stretcher or other means is provided by which the subject may be positioned in the cavity. An electric heating cable on the exterior of the wall member heats the member in a highly uniform manner and efficiently and effectively radiates heat to the subject. Electric circuitry is connectable to a source of electric power for energizing and controlling the electric heating cable.

The wall member is typically a cylindrical copper sheet closed at one end and containing sealing doors at the other, through which the body of the patient is received in the cavity. The electric heating cable is applied in a uniform pattern over the cylindrical sheet and covered with insulation. The cable is preferably a plurality of segments energized in parallel to provide low density, uniform radiant heat sufficient to raise the core temperature to the desired level during an appropriate time period while avoiding burns or other skin injury, as from localized hot spots.

The apparatus provides close control of temperature and a high degree of repeatability. Temperature sensors are included in the circuitry for controlling the energization of the electric heating cable responsive to wall member temperature and to desired and maximum permissible temperatures in the chamber.

The present invention is low in cost with respect to both apparatus costs and treatment costs. It is anticipated that the present invention will permit elimination of general anesthesia to the patient. This will reduce the attendant requirements for highly specialized personnel and facilities and permit carrying out hyperthermic treatment with a smaller number of people trained in hyperthermia.

While the present invention is described herein in the context of hyperthermic treatment of cancer it will be appreciated that other applications may well arise. For example, the apparatus may be used to treat victims of exposure by safely restoring their depressed body temperatures to the normal level. The possibility of its use in the treatment of diseases of the joints also comes to mind.

Figure 1:
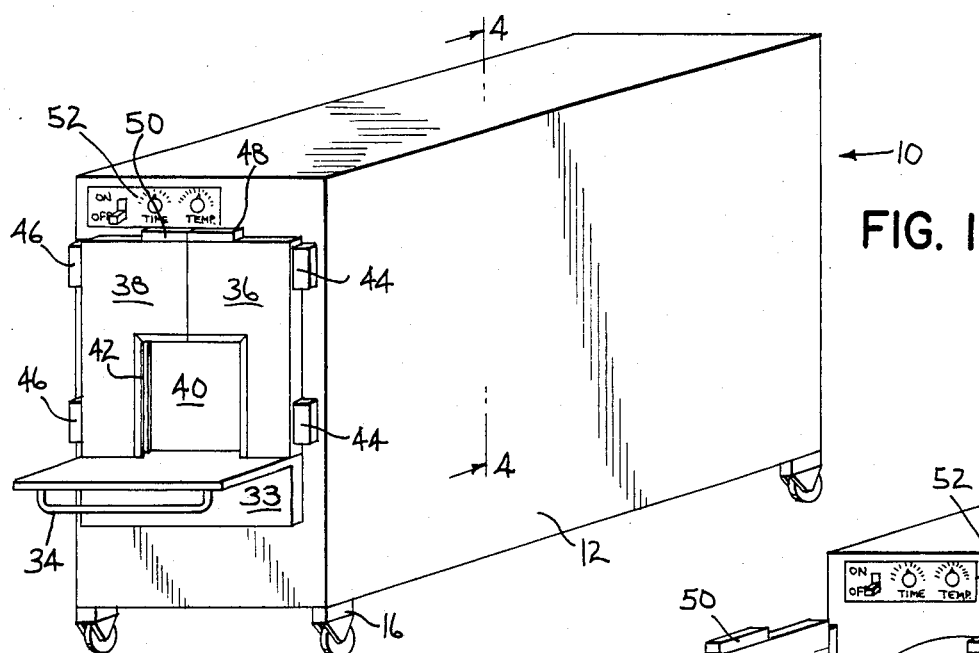
FIG. 1 is a perspective view of the radiant heat body heating unit of the present invention.
Figure 2:
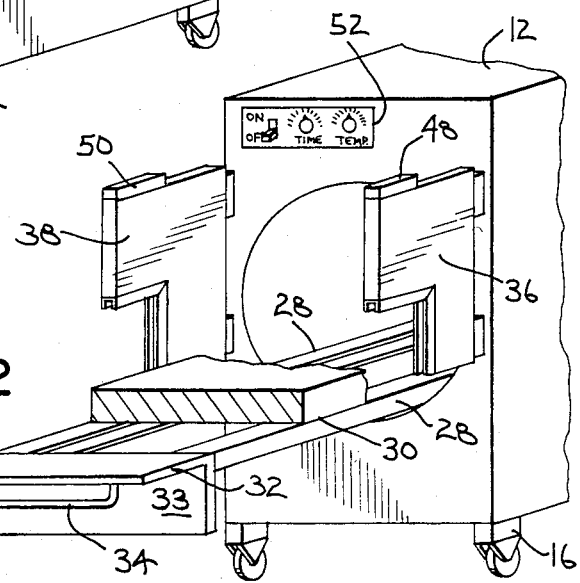
FIG. 2 is a fragmentary perspective view of the unit showing additional details thereof.

FIG. 1 shows apparatus 10 of the present invention for raising the internal or core temperature of live animals, particularly mammalian subjects, including humans. Apparatus 10 includes housing 12 mounted on framework 14, shown most clearly in FIGS. 3 and 4. Framework 14 includes coasters 16 lending mobility to the unit.

Wall member 18 is supported by framework 14. As shown most clearly in FIG. 3, wall member 18 includes wall 20 sealed by disc 22 at one end to form a tubular chamber 24 in which the subject or a selected portion of the subject, such as his/her body is received, as hereinafter described. The cylindrical configuration of wall 20 assists in even heat distribution in chamber 24. Wall member 18 is preferably formed from sheet copper material so that the member has an emissivity that enhances its effectiveness as a radiator. Copper is a good uniform conductor of heat helping to avoid localized hot spots and skin burns to the subject. Copper also has good heat retention properties providing consistent temperatures by avoiding sudden temperature changes.

Figure 3:
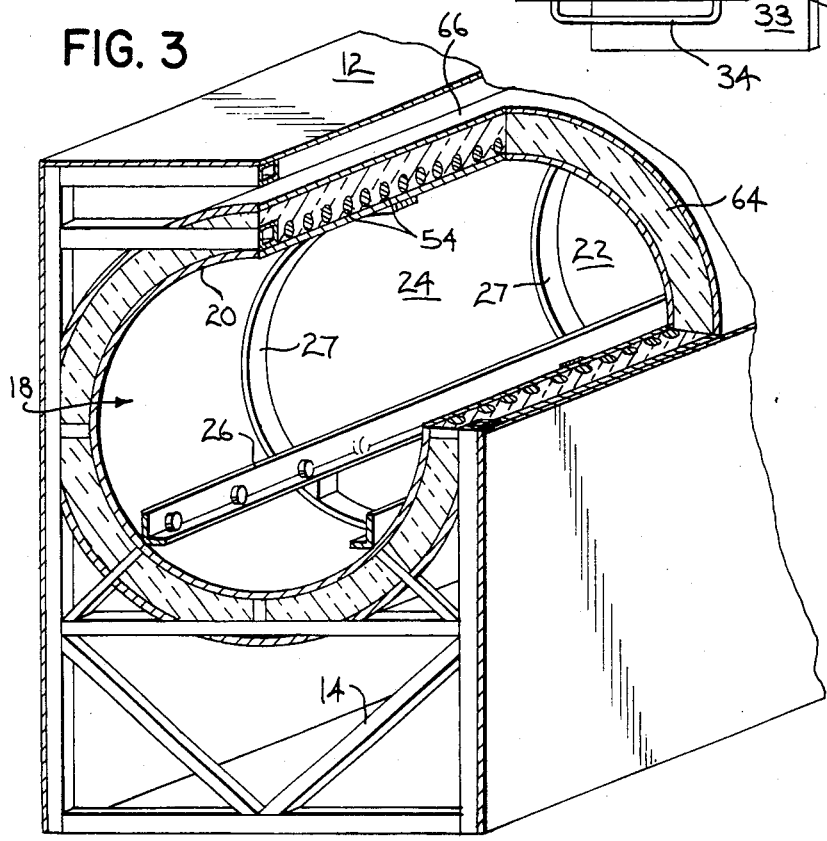
FIG. 3 is a partially cut-away perspective view of the unit.

Rails 26 are positioned on wall member 18 for receiving carriage 28 for stretcher 30 on which the subject is placed. Rails 26 may be mounted on bands 27 that extend around the interior of wall 20 in the middle and rear of chamber 24, as shown in FIG. 3. Bands 27 may be expanded by toggle mechanisms, not shown to clamp the bands, and hence rails 26, to wall 20. The use of bands 27 avoids the need to puncture wall 20 and the need for seals and the like to maintain the integrity of chamber 24. The cleaning of chamber 24 is also facilitated since bands 27 and rails 26 can be removed from chamber 24.

Carriage 28 includes head rest 32 for the subject, a panel 33 that assists in closing chamber 24, and a handle 34 by which the carriage, stretcher, and subject are moved into and out of chamber 24.

The open end of wall member 18 is closed by a pair of insulated doors 36 and 38 forming opening 40 through which the neck of the patient extends so that his/her head can rest on head rest 32. Doors 36 and 38 are shaped as an inverted L and have retaining means such as channel 42 for receiving a sealing collar 43 that goes around the neck of the patient to seal opening 40. The doors are sealed at the bottom by head rest 32. Doors 36 and 38 are provided with hinges 44 and 46 along outer edges and held closed by magnetic latches 48 and 50 at their inner edges. Doors 36 and 38 and head rest panel 33 may be provided with gaskets that seal these elements to wall member 18 or housing 12 when they are closed. Because the head rest 32 is coupled to stretcher 30 and because L-shaped doors open in the center, the insertion and, particularly, removal of the subject and associated medical equipment and instrumentation from chamber 24 is facilitated. In emergencies with humans, the patient can be removed from chamber 24 by pulling handle 34 outwardly and allowing the patient's shoulders to swing open doors 36 and 38.

Figure 6:
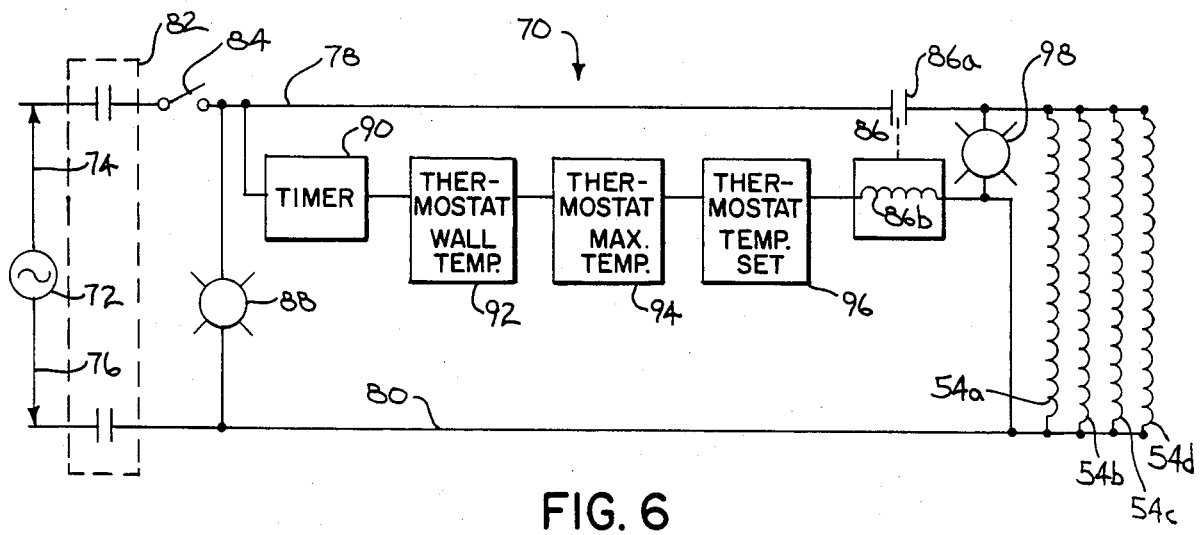
FIG. 6 is a schematic diagram showing circuitry for energizing the electric heating cable.
Figure 7:
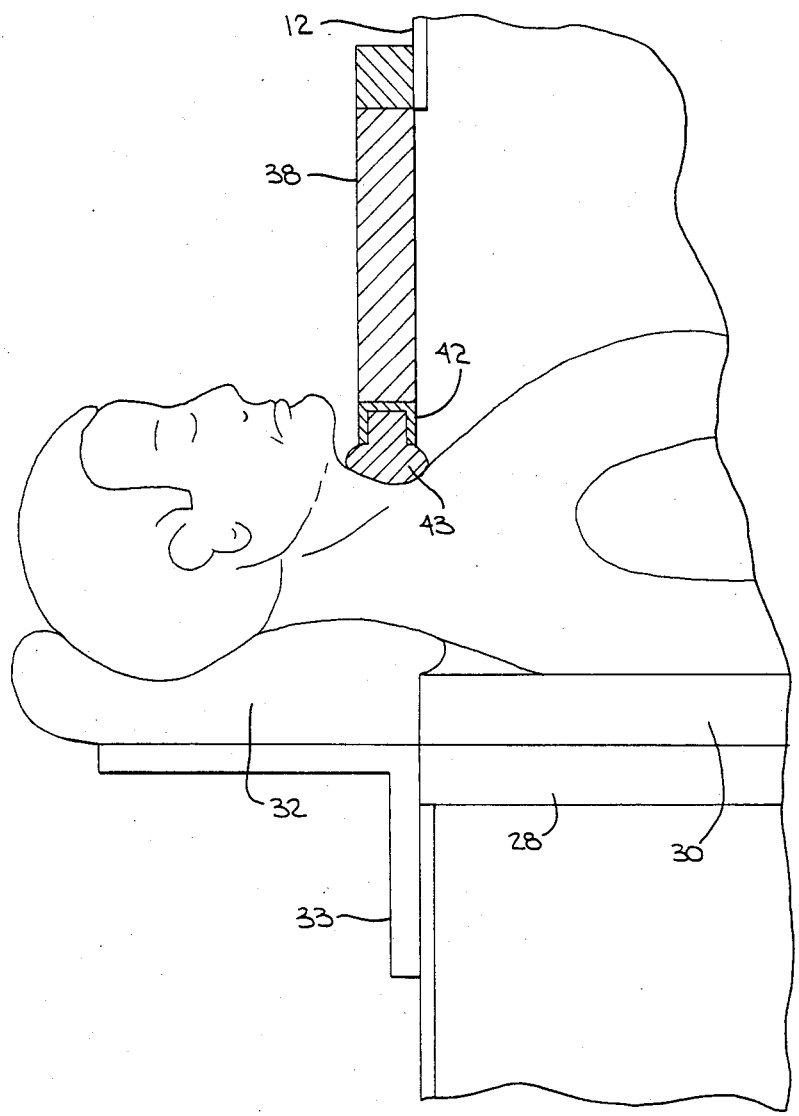
FIG. 7 is a fragmentary cross-sectional view of the unit and a human subject.

Housing 12 includes control panel 52 for the electrical circuitry shown in FIG. 6.

Figure 5:
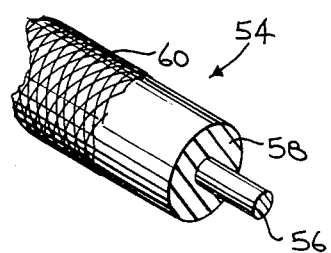
FIG. 5 is a cut-away view of an electric heating coil suitable for use in the present invention.

Means are provided on wall member 18 to heat the wall member and chamber 24. As shown in the Figures, such means may comprise electric heating cable 54 wrapped about the exterior of wall 20 so that the wall member can assist in diffusing the heat from the cable. The cable may be wrapped circumferentially, as shown in FIG. 3 and the turns spaced along the periphery of the wall member to provide uniform heating to the wall member to avoid establishing localized hot spots on wall member 18. The turns of cable 54 will typically be uniformly spaced along wall 20, possibly with minor variations because of frame 14 or other localized anomalies. A retaining or spacer means, not shown, may be provided to hold cable 54 in position on wall 20. Cable 54 is available from several sources including the Continental Wire and Cable division of Anaconda Copper Co. and the Wire and Cable Division of the General Electric Company. As shown in FIG. 5, cable 54 may comprise an internal metal resistance wire 56; an asbestos, plastic, or rubber sheath 58 surrounding and insulating the wire; and an outer braided metal jacket 60 for armoring and electrically grounding the cable. Electric resistance wire 56 may be a single conductor of 19 or 20 gauge having a resistance of approximately 675 ohms per circular mil foot at 20° C. The conductor is surrounded by 0.045 inch thick silicon rubber sheath 58 and a nickel plated copper shield braid.

The heating of wall member 18 by the heating means, such as cable 54, is subject to two, somewhat divergent, considerations. A sufficient quantity of radiant heat must be provided from wall member 18 to raise the core temperature of the subject in chamber 24 by a physiologically significant amount in a desired period of time. A physiologically significant temperature increase may be that necessary to cause the subject to enter the hyperthermic state. In accordance with this consideration, cable 54 may provide a heat input sufficient to raise the core temperature of the subject at least 4° C. within a period of 120 minutes by the radiant heat in chamber 24. More particularly the apparatus should be capable of raising the core temperature of the subject 4° to 5° C. in a period of 60 to 120 minutes.

At the same time, however, the density of heating, or heat output per unit area of wall member 18, should be sufficiently uniform and low as to minimize the possibility of superficial injury to the subject, such as burns, from wall temperature conditions, and particularly from localized hot spots in the wall member.

The weight of the subject may serve as a factor in the selection of the heat input from the electric heating means. For heating animal subjects having a weight of 70 kg (154 lbs) in an appropriately sized chamber 24, an electric heating cable having a power rating of about 1,000 watts has been employed.

Figure 4:
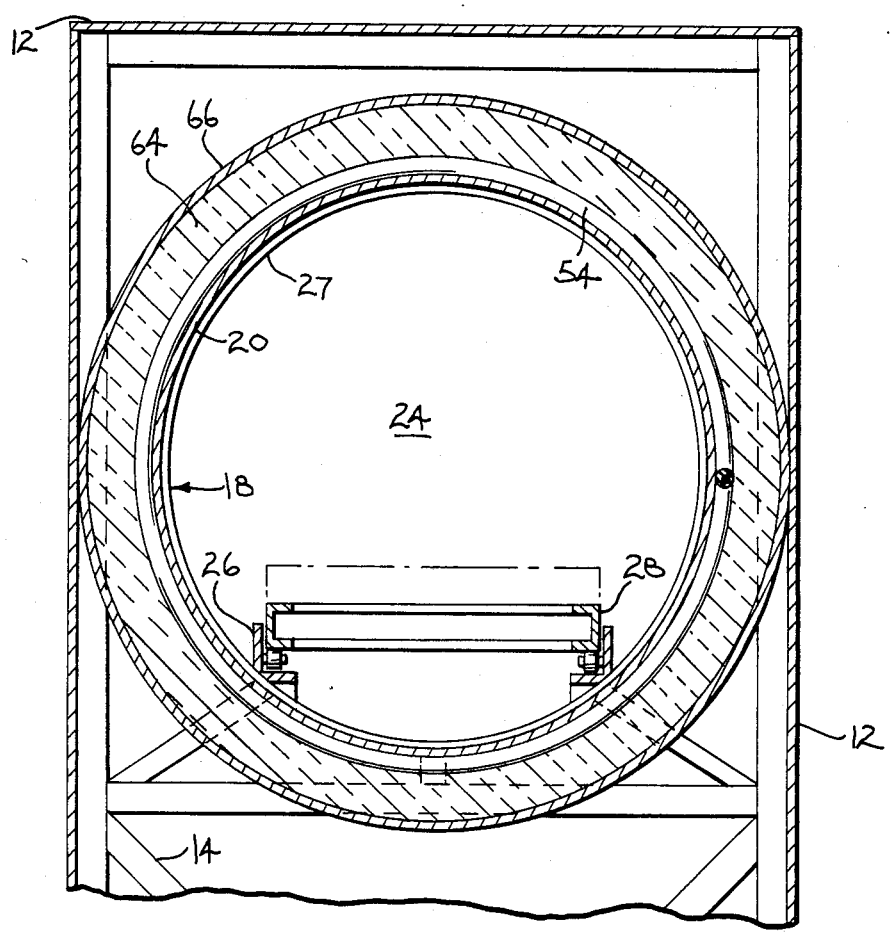
FIG. 4 is a cross-sectional view taken along the line 4—4 of FIG. 1.

As shown most clearly in FIG. 4, tubular wall member 18 and cable 54 are surrounded by an insulating material 64 such as glass fiber insulation, that is held on tubular member 18 by wrapper 66 formed of metal or other material.

Electrical circuitry for energizing heating cable 54 is shown in FIG. 6. Heating cable 54 is preferably divided into a plurality of segments connected in parallel to insure even heating throughout tubular chamber 24. This may be accomplished by the appropriate electrical connection of taps along the heating cable. FIG. 6 shows, for exemplary purposes, heating cable 54 divided into four quarter segments 54a, 54b, 54c, and 54d.

Circuitry 70 is connectable to an a.c. power source 72, such as conventional 120 volt, 60 cycle alternating current supply 72 having energized line 74 and neutral line 76. Conductors 78 and 80 of circuitry 70 are connected to lines 74 and 76 and contain ground fault interrupter 82 requiring manual reset. Ground fault interrupter 82 deenergizes circuitry 70 in the event of an electrical failure to lessen or avoid shock hazards in apparatus 10. Conductor 78 contains power switch 84 and relay contacts 86a, which when closed, permit parallel energization of heating cable segments 54a through 54d through conductor 80.

Indicator lamp 88 is connected across lines 78 and 80 to indicate when main power switch 84 is closed.

A plurality of elements are also connected across lines 78 and 80 to control the operation of electric heating cable 54. These include timer 90 by which the time period of energizing cable 54 may be established. Thermostat 92, which may be of the normally closed, bimetallic type is placed on wall 20 of wall member 18 to sense the temperature of the wall for deenergizing electric cable 54 in the event the temperature rises above a desired maximum value. Typically thermostat 92 will be set to open at 60° C. (140° F.) and reclose at 54° C. (130° F.) and is preferably not operator accessible or adjustable. Limiting the wall temperature to this magnitude lessens or avoids the danger of skin burns from apparatus 10. Thermostat 94 may be mounted in tubular chamber 24 at a location appropriate to sense the temperature inside the chamber. Thermostat 94 may be of the normally closed, fluid expansion type. It is not operator adjustable but is preset to open at the maximum temperature desired in the chamber. This is typically 70° C. (160° F.). The thermostat will close at 68° C. (155° F.) and below. Thermostat 96 is also placed in tubular chamber 24 at a location to sense the temperature in the chamber. Thermostat 96 may also be of the normally closed, fluid expansion type and is adjustable by the operator to establish a selected temperature in the chamber less than the maximum temperature established by thermostat 94. The coil 86b of relay 86 is connected in series with timer 90 and thermostats 92, 94, and 96 across lines 78 and 80. Coil 86b operates contacts 86a in line 78. Indicator lamp 98 indicates when relay contacts are closed and heating cable 54 is energized.

In use, the patient may be prepared for hyperthermic treatment in apparatus 10 by light sedation. The temperature indicators necessary to monitor internal temperature will be placed in the patient, as for example, through the use of rectal, esophageal, and/or cardiac probes. Sensors for other physiological functions, such as respiration and heart beat rate, are also applied to the patient.

The patient will be placed on stretcher 30 with his/her head resting on headrest 32. The patient is slid into tubular chamber 24 on stretcher 30 with his/her head outside chamber 24. Doors 36 and 38 are closed and collar 43 placed around the neck of the patient to tightly seal opening 40 making chamber 24 a closed system. Timer 90 is set for the maximum treatment time. Thermostat 96 is set for the maximum temperature desired in chamber 24. Power switch 84 is closed to energize heating cable 54. The contacts of timer 90, the thermostats 92, 94, and 96 are closed, energizing relay coil 86b of relay 86 and closing relay contacts 86a. This permits energization of electric cable 54. The energization of cable 56 heat copper wall member 18 radiating heat to the patient on the stretcher. The internal or core temperature of the patient is monitored through the temperature probes. The temperatures obtained from the rectal temperature probe are typically considered the core temperature of the patient for treatment purposes. The sealing of opening 40 by collar 43 causes the perspiration of the patient to maintain a condition of saturation or near saturation in chamber 24 limiting patient heat loss by evaporation. Fluids lost through perspiration are restored intravenously. As the temperature of the patient increases, his/her metabolic heat generation increases substantially to supplement the radiant heat from wall member 18 in attaining the hyperthermic state.

When the desired core temperature is reached in the patient, the patient may be removed from tubular chamber 24 and covered with a blanket to minimize evaporative heat losses. Through the loss of thermo-regulatory capability brought about by the hyperthermic condition, the desired internal temperature of the patient is maintained by the heat generated by increased metabolic activity without the need for external heat application. When the patient has remained in the hyperthermic condition for the desired period of time, the blanket is removed to allow cooling by evaporation and the restoration of normal temperature regulation. Should the patient require additional cooling to terminate the hyperthermic condition, this may be achieved by a cooling blanket or an alcohol sponge bath.

A typical test of apparatus 10, utilized a 70 kg (154 lb) pig as an animal subject. Such an animal subject resembles a human in body weight, fat distribution and in cardic, liver and respiratory physiology. It, however, does not perspire. The animal, appropriately instrumented, was placed in apparatus 10 and heating cable 54 energized. The internal or core temperature of the animal, measured rectally, was raised to 41.8° C. in about 80 minutes. Skin temperature rose to 42.5° C. Air temperature near the wall did not exceed 65° C. (149° F.) while adjacent to the animal, the temperature was 46° C. (114° F.). The pig was then removed from apparatus 10 and hyperthermic conditions maintained for two additional hours at the end of which the internal temperature was 41.6° C. The experiment was then terminated by a liberal ethanol bath. In about 90 minutes internal temperature fell to 38° C. (100° F.).

Tests of the above described type suggest the suitability of the present invention for use with humans.

Various modes of carrying out the invention are contemplated as being within the scope of the following claims particularly pointing out and distinctly claiming the subject matter which is regarded as the invention.

I claim:

1. Whole body hyperthermia apparatus capable of providing hyperthermic core temperature conditions in live mammalian subjects while minimizing risk to the subject comprising:

a wall member and a pair of end walls defining a closed cavity suitable for receiving the body of the subject with the head and neck of the subject extending through an opening in one of said end walls outside the closed cavity, said one end wall having closure means at said opening for providing a substantially air tight seal at said opening about the neck of the subject to prevent air circulation to and from said cavity, said wall member extending completely around the body of the subject when received therein, said wall member being formed of a material capable of radiating heat and having a radiant heat enhancing emissivity;

means for positioning the body of the subject in a generally central position in the cavity;

electric heating means mounted on the exterior of said wall member generating a heat input to the wall member for providing a sufficient quantity of radiant heat from the wall member directly to the body of the subject to increase the core temperature of the subject by radiant heating by a physiologically significant amount in a desired period of time, said wall member and heating means providing such radiant heat generally uniformly over the entire area of the wall member to minimize convection air currents in said cavity and at a power density low enough to limit the temperature of the air near said wall member at approximately 65° C. and the skin temperature of the subject at approximately 42.5° C. while achieving a hyperthermic condition of approximately 41.8° C. as measured rectally in the subject; and circuit means connected to a source of electrical power for energizing said electric heating means.

2. The apparatus according to claim 1 wherein said apparatus is further defined as one for obtaining core temperature increases to hyperthermic conditions in the subject and wherein said electric heating means is further defined as providing a heat input to the wall member sufficient to attain hyperthermic conditions in the subject.

3. The apparatus according to claim 1 or 2 wherein said wall member is formed of a cupreous material.

4. The apparatus according to claim 1 wherein said electric heating means is further defined as generating a heat input sufficient to raise the core temperature of the subject at least 4° C. within a period of 120 min.

5. The apparatus according to claim 4 wherein said electric heating means is further defined as generating a heat input sufficient to raise the core temperature of the subject 4° to 5° C. in a period of 60 to 120 min.

6. The apparatus according to claim 1 wherein said heating means is applied in a generally uniform manner to said wall member.

7. The apparatus according to claim 6 wherein said electric heating means comprises an electric heating cable applied in a uniform pattern to the wall member.

8. The apparatus according to claim 7 wherein said electric heating cable comprises a plurality of cable segments electrically connected in parallel.

9. The apparatus according to claim 1 wherein said electric heating means comprises an electric heating cable applied in a generally uniform pattern to at least a selected portion of said wall member.

10. The apparatus according to claim 9 wherein said electric heating cable comprises a plurality of cable segments electrically connected in parallel.

11. The apparatus according to claim 1 wherein said electric heating means comprises an electric heating cable having a power rating of approximately 1000 watts.

12. The apparatus according to claim 1 including insulation means on the exterior of said wall member and electric heating means for assisting in the uniform heating.

13. The apparatus according to claim 1 wherein said electric circuit means includes control means responsive to the temperature in said cavity for establishing that temperature at a desired level.

14. The apparatus according to claim 13 wherein said electric circuit means includes further control means responsive to the temperature in said cavity for establishing the maximum temperature in said cavity.

15. The apparatus according to claim 14 wherein said electric circuit means includes additional control means responsive to the temperature of said wall member for establishing the maximum temperature of said wall member.

16. The apparatus according to claim 13 wherein said electric circuit means includes additional control means responsive to the temperature of said wall member for establishing the maximum temperature of said wall member.

17. The apparatus according to claim 1 wherein said electric circuit means includes control means responsive to the temperature in said cavity for establishing the maximum temperature in said cavity.

18. The apparatus according to claim 1 wherein said electric circuit means includes control means responsive to the temperature of said wall member for establishing the maximum temperature of said wall member.

19. The apparatus according to claim 1 wherein said electric circuit means includes means for establishing the period of energization of said electric heating means.

20. The apparatus according to claim 1 wherein said wall member is generally cylindrical.

21. The apparatus according to claim 1 wherein said closure means includes a pair of doors positioned across an end of said cavity and having abutting edges located generally centrally of said wall member and wherein said doors are openable along said abutting edges.

22. The apparatus according to claim 1 wherein said positioning means comprises a stretcher for receiving the head and body of the subject, said stretcher having means extending from said cavity by which the the body of the subject may be inserted and removed from said cavity.

23. The apparatus according to claim 22 wherein said stretcher forms a portion of said closure means.

* * * * *